Figure 1:
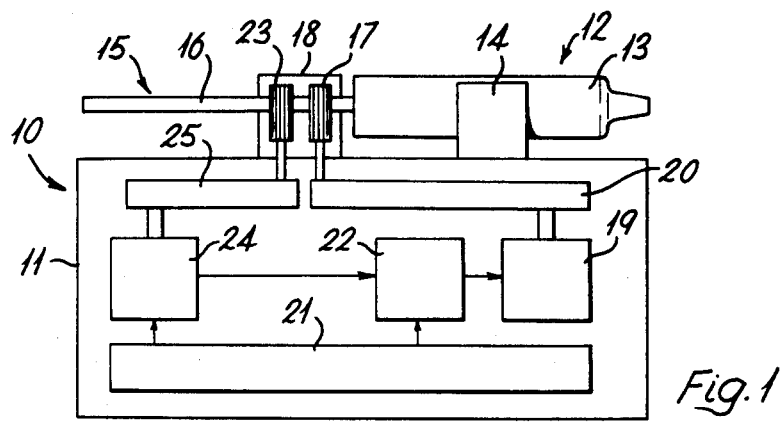

United States Patent [19]

Sutherland et al.

[11] Patent Number: 4,620,848
[45] Date of Patent: Nov. 4, 1986

[54] POWERED INFUSION APPARATUS

[75] Inventors: Ian A. Sutherland, Harpenden; Geoffrey R. Chambers, Northwood, both of England

[73] Assignee: National Research Development Corporation, London, England

[21] Appl. No.: 777,073

[22] Filed: Sep. 17, 1985

[30] Foreign Application Priority Data

Sep. 19, 1984 [GB] United Kingdom ................ 8423749

[51] Int. Cl.$^4$ .............................................. A61M 5/00
[52] U.S. Cl. ............................ 604/154; 128/DIG. 12; 604/246
[58] Field of Search .................. 604/154, 131, 246; 128/DIG. 1, DIG. 12, DIG. 13

[56] References Cited

U.S. PATENT DOCUMENTS

| 3,395,704 | 8/1968 | Frey et al. | 604/154 |
| 4,085,747 | 4/1978 | Lee | 604/154 |
| 4,090,502 | 5/1978 | Tajika | 128/DIG. 12 |
| 4,300,554 | 11/1981 | Hessberg et al. | 128/DIG. 12 |
| 4,416,662 | 11/1983 | Dore et al. | 604/154 |
| 4,465,474 | 8/1984 | Mardorf et al. | 604/154 |
| 4,502,488 | 3/1985 | Degironimo et al. | 604/246 |

FOREIGN PATENT DOCUMENTS 2077599  8/1984  United Kingdom ................ 604/154

Primary Examiner—Stephen C. Pellegrino
Assistant Examiner—John Ferros
Attorney, Agent, or Firm—Cushman, Darby & Cushman

[57] ABSTRACT

Apparatus for powered infusion or sampling of a patient comprises: a housing (11) carrying a toothed roller (17), an electric motor (19), a transmission (20) operably coupling such roller and motor, and attachment means (14); and a syringe (12) including a barrel (13) and plunger (15), the plunger being of plastics material having a smooth untoothed longitudinal profile (16), and the attachment means holding the syringe by its barrel in a predetermined disposition relative to the housing with the plunger extending transversely relative to the toothed roller axis of rotation and such roller in penetrated driving engagement with said plunger profile; is provided with a further roller (23) carried by said housing and in transversely driven engagement with the syringe plunger; and a monitor (24) operably coupled with the further roller to generate electrical signals representing rotation of such roller and, in turn, plunger translation. The further roller can be toothed and in similar penetrated engagement with the plunger as the first toothed roller, and the two rollers can be mutually arranged coaxially across, serially along or in opposition about the plunger.

10 Claims, 5 Drawing Figures

POWERED INFUSION APPARATUS

This invention concerns powered infusion apparatus and more particularly such apparatus of the kind according to GB Pat. No. 2077599.

Various proposals have been made for powered infusion apparatus and one category of these proposals involves the provision of compact devices which are readily portable on a patient's body and operable to provide from a single charge of medicant a prescribed infusion schedule over a period of up to a day or more. Such a schedule can involve steady, intermittent or other infusions dependent on the patient condition and treatment in question. The proposals in this category mostly involve the use of a syringe which is to be coupled to the patient by way of a cannula while the syringe is held by its barrel in the apparatus and operated by a drive mechanism including an electric motor. Typically the motor operates the syringe through a gear train terminating in a leadscrew or rack which pushes the syringe plunger into the barrel continuously or in incrementally stepped manner.

Practical deployment of these proposals normally requires the adoption of some measure for monitoring the operation of the syringe. This is appropriate not only to control the operation so that this occurs in a desired manner, but also to provide a basis for indicating when any significant non-operational event occurs. A non-operational event will of course occur when the syringe plunger reaches the end of the barrel and the patient should be made aware of the need for recharging or syringe replacement. Also, non-operation can occur due to the inability of the syringe drive to overcome a cannula constriction or some other resistance and, again, the patient should be made aware of this.

Normally, monitoring for these purposes can be based on repetitive signal generation under the control of rotation of an element in the gear train. However, this is now thought deficient for apparatus of the kind according to Pat. No. 2077599.

Apparatus of this kind comprises: a housing carrying a toothed roller; an electric motor; a transmission operably coupling said roller and motor; a syringe including a barrel and plunger, said plunger being of plastics material and having a smooth untoothed longitudinal profile; and means releasably holding said syringe in a predetermined disposition relative to said housing with said plunger extending transversely to the axis of rotation of said roller in penetrated driving engagement with said plunger profile.

It will be appreciated that, in the operation of this last apparatus, the toothed roller effectively cuts a rack in the syringe plunger to drive the same whereas other apparatus in the same category relies on the use of gear members which are preformed. This gives rise to the possibility of an additional significant non-operational event with the former apparatus which is, relatively speaking, effectively negligible in the case of the latter apparatus, namely, the cutting out by the toothed roller of plastics material from the syringe plunger to the extent that syringe operation is no longer possible. Such cutting out will not necessarily be detected by existing monitoring facilities becuase it is implicit that the transmission will continue to operate without driving the syringe plunger.

An object of the present invention is to improve this situation and, to this end, apparatus of the kind in question has a further roller with its axis of rotation transverse to and in driven engagement with said plunger, said further roller being operably coupled to a monitor for generating electrical signals representing rotation thereof, and, therefore, movement of said plunger.

Normally the further roller will, like the first-mentioned roller, also be toothed and in penetrated engagement with said plunger profile or a further such profile. However this is not essential as the further roller may be of a friction form driven by the plunger.

It will, of course, be evident that the invention serves not only to provide a monitoring facility in respect of the additional event referred to above, but also events common to other apparatus in the same category.

In a preferred form of apparatus according to the invention the two rollers respectively in driving and driven engagement with the syringe plunger are disposed on mutually opposite sides of the plunger. This is additionally advantageous in reducing friction in the driving operation because, in the absence of opposed rollers, the plunger driving roller will normally be opposed by a pressure pad or other pressure-applying means across which the plunger must move against frictional resistance.

Figure 2:
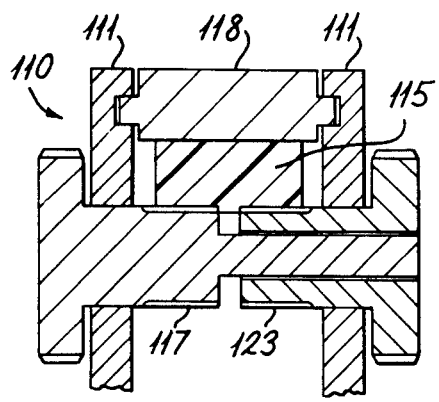
Figure 3:
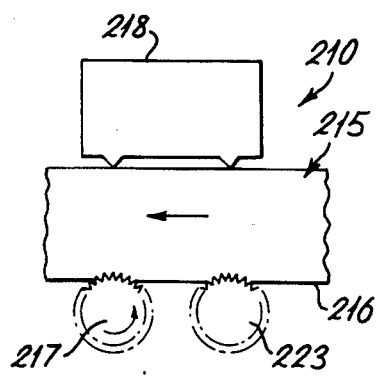
Figure 4:
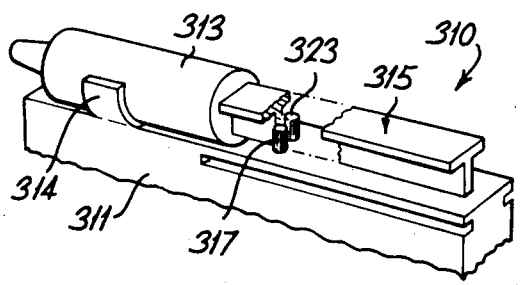
Figure 5:
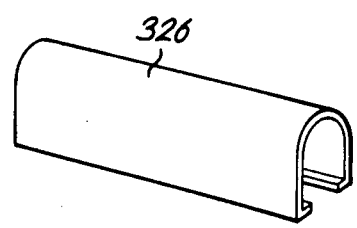
Figure 5:
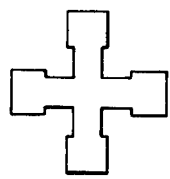

In order to clarify the invention in respect of different forms thereof, the same will now be described, by way of example, with reference to the accompanying drawings, in which:

FIG. 1 schematically illustrates apparatus according to the invention,

FIGS. 2 to 4 partially illustrate three respectively different forms of such apparatus, and FIG. 5 illustrates in cross-sectional view a modified syringe plunger for the form of the invention in FIG. 4.

The apparatus of FIG. 1 is denoted generally by the reference numeral 10 and comprises a housing 11 on which a syringe 12 can be held releasably in a predetermined disposition. The syringe is held by its barrel 13 with a strap, clip or other attachment means 14 secured with the housing. The syringe plunger 15 has a smooth untoothed longitudinal profile 16 and, in the afore-mentioned disposition, this plunger extends across the housing with such profile engaged by a toothed drive roller 17 carried by the housing. The plunger is disposed transversely to the axis of rotation of the roller and their inter-engagement involves penetration of the roller teeth into the plunger profile 16, such penetration being assured by a pressure pad 18 releasably locatable to engage the plunger in opposition to the roller.

The roller 17 is operably coupled with an electric motor 19 through a geared transmission 20, the motor being energisable from a battery power source 21 by way of a control circuit 22. The motor, transmission, power source and control circuit are also carried by the housing.

As so far described this apparatus accords with Pat. No. 2077599, operation being such that the roller translates the plunger into the syringe barrel to dispense a medicant. More specifically the control circuit is effective to render this operation incremental with the frequency of this operation being adjustable to predetermine the rate at which the syringe is discharged.

According to the present invention the housing carries a further roller 23 operably coupled with a monitor 24 by way of a further geared transmission 25. The further roller, like the first-mentioned roller, has its axis of rotation transverse to the plunger and is engaged with the plunger. Also the further roller can be toothed and in penetrated engagement with the plunger profile 16 or an equivalent profile. In any event the further roller is arranged such that driven translation of the plunger by the first roller will in turn cause rotation of the further roller and this will activate the monitor. The monitor itself is operable to generate electrical signals representing rotation by the further roller.

Clearly a basic function served by the monitor is the indication, by way of the absence of its signals, that plunger movement is not occurring in circumstances in which the apparatus is otherwise operating. Such an indication can involve the generation of an alarm such as by way of a visual and/or aural signal.

The monitor can additionally serve in the plunger movement control by providing repetitive signals representing uniform incremental plunger movements. For this purpose the monitor typically involves an apertured rotary member driven by the further roller and interposed between a light source and photodetector, or some equivalent arrangement.

FIGS. 2 to 4 in employ corresponding reference numerals to those of FIG. 1 but with the addition of successive hundreds digits for purpose of distinction from figure to figure.

FIG. 2 shows, in transverse cross-section relative to the syringe therein, that part of the apparatus housing 111 where the syringe plunger 115 is penetratingly drivably engaged between the toothed roller 117 and the opposed pressure pad 118. The teeth of the roller 117 do not extend wholly across the width of the plunger, but only partway across with the roller thereafter being reduced in diameter to a shaft which rotatably carries the further toothed roller 123, this last roller being of corresponding external diameter to roller 117.

In this form of the invention the syringe plunger preferably has a cross-sectional shape which is at least partially rectilinear in outline to correspondingly penetratingly engage both the driving and driven toothed rollers 117 and 123.

The benefits of this form of the invention are that it is compact in its deployment of the further toothed roller and allows retention of a general configuration which may already have been adopted for use of Pat. No. 2077599. The compaction obtained by mounting the driven roller on the drive one will, of course, given rise to a need for care to avoid seizure of the two rollers due to corrosion. Also, the drive must still overcome the friction arising from the use of a pressure pad to sustain the plunger/roller engagements.

FIG. 3 is seen to involve location of the driven roller 223 in engagement with the same longitudinal profile 216 of the plunger 215 as the drive roller 217. More specifically, the driven roller is located alongside the drive roller, but behind the same relative to the direction of plunger movement (denoted by arrow) into the syringe. Again, penetrated engagement of the plunger is sustained by the use of a common pressure pad 218, although the effect of this pad may be biased towards the drive roller to lighten the load at the driven roller and optimise the drive force on the plunger.

As with the form of FIG. 2, the form of FIG. 3 is relatively compact and allows retention of a preceding general configuration, but without risk of seizure between the rollers. Also, the syringe plunger can have any cross-sectional shape suitable for use with a single penetratingly engaged roller. Against these benefits, it is likely that increased friction will occur for a given drive force on the plunger.

FIG. 4 is seen to involve location of the drive and driven toothed rollers 317 and 323 in opposition about the plunger 315.

This is seen immediately to be beneficial by omission of a pressure pad, the function of which is served by the added driven roller, with a consequent reduction in frictional forces.

It may be thought this benefit is off-set by the fact that secure location of the syringe is problematical because it is now to be loaded axially of the rollers rather than transversely held against a single roller by a pressure pad, and also that the transverse sequence of roller, plunger and roller acts against compaction by requiring undue width, but this is not so. The syringe can be held in position by a cover, as indicated at 326, which is located longitudinaly over the plunger and adjacent end of the syringe barrel by sliding engagement with the main body of the housing 311, the cover serving additionally to keep dust and other foreign material from the rollers. As to compaction in width: the rollers need not be of large diameter because they will, in any case, be coupled with geared transmissions which respectively step down from the motor to the drive roller 317 and step up from the driven roller 323 to its monitor; while the plunger suitably has a cross-sectional form involving a general T-shape with its stem engaged between the rollers and its bar thereover, such shaping being adequately stiff without undue material bulk.

In this last respect it is presently preferred that the T-shape has the free end portion of its stem transversely enlarged. With this last shape, the drive load at which material is cut out from the plunger can be predetermined by choice of the extent of the enlarged portion, longitudinally of the stem, while the depth of toothed roller engagement in the plunger can be controlled by choice of the extent of the enlarged portion transversely of the stem. Also it may be preferred to employ a plunger of cruciform cross-section of which any arm can form the T-shape stem, such cross-section being shown in FIG. 5 together with the enlargement just-mentioned at the free end of each arm.

It may also be preferred for the form of roller arrangement in FIG. 4 that the syringe be located in a predetermined disposition, such as by keying of its plunger in a complementary seating, in a cover adapted by hinging or other mechanism to connect with the housing and at the same time locate the plunger in the desired engagement between the rollers.

It will be appreciated from the above description that the invention is amenable to practical deployment in various forms although, as indicated earlier, the form of FIG. 4 presently appears preferable.

Also, while the invention is applicable to apparatus involving continuous or incremental step driving modes, it is particularly useful with the latter mode because, by its very nature, there is an increased risk of error or failure in the drive performance and the associated control should accordingly be as rigorous as possible. Clearly the invention attains this last objective better than is the case in the prior art to the extent that the former depends explicitly on syringe operation whereas the latter does not.

Lastly while the invention has been described with reference to infusion, this being the predeominant prospective application, the invention is also useful in application to the sampling of body fluids from patients.

We claim:
1. Apparatus comprising:

a housing carrying a toothed roller, an electric motor, a transmission operably coupling said motor to drive said toothed roller, a further roller, a monitor operably coupled with said further roller to generate electrical signals representing rotation of such roller and attachment means; and a syringe including a barrel and plunger;

said plunger being of a plastics material having a smooth untoothed longitudinal profile, and said attachment means releasably holding said syringe by said barrel in a predetermined disposition relative to said housing with said plunger extending transversely to the axes of rotation of said rollers, with said toothed roller in penetrated driving engagement with said plunger profile, and with said further roller in driven engagement with said plunger.

2. Apparatus according to claim 1 wherein said further roller is toothed and in penetrated driven engagement with said plunger profile or a further such profile.

3. Apparatus according to claim 1 comprising a pressure-applying means locatable to engage said plunger in opposition to said rollers.

4. Apparatus according to claim 3 wherein said roller axes are mutually coaxial.

5. Apparatus according to claim 3 wherein said roller axes are mutually parallel and said rollers are positioned mutually serially relative to said plunger.

6. Apparatus according to claim 5 wherein said toothed and further rollers are positioned respectively nearer to and further from said barrel.

7. Apparatus according to claim 5 wherein said pressure-applying means is biassed in opposition to said toothed roller.

8. Apparatus according to claim 1 wherein said rollers are positioned in mutual opposition about said plunger.

9. Apparatus according to claim 8 wherein said rollers project axially outwardly from said housing in mutally parallel manner, and said plunger has at least one T-shape in cross-section of which the stem is engaged betweeen said rollers and the cross bar is located over the outer axial ends of said rollers.

10. Apparatus according to claim 9 comprising a cover releasably connectable with said housing to hold said plunger in engagement with said rollers.

* * * * *